US008195269B2

(12) United States Patent
Bogoni et al.

(10) Patent No.: US 8,195,269 B2
(45) Date of Patent: Jun. 5, 2012

(54) SYSTEM AND METHOD FOR AUTOMATIC DETECTION AND MEASUREMENT OF MALACIA IN THE AIRWAYS

(75) Inventors: Luca Bogoni, Philadelphia, PA (US); Gerardo Hermosillo Valadez, West Chester, PA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1254 days.

(21) Appl. No.: 11/772,379

(22) Filed: Jul. 2, 2007

(65) Prior Publication Data

US 2008/0009683 A1  Jan. 10, 2008

Related U.S. Application Data

(60) Provisional application No. 60/819,424, filed on Jul. 7, 2006.

(51) Int. Cl.
*A61B 5/00* (2006.01)
*A61B 5/055* (2006.01)
*A61B 6/00* (2006.01)
*A61B 8/00* (2006.01)

(52) U.S. Cl. ........ 600/407; 600/410; 600/425; 600/437; 600/529; 600/533; 382/128; 382/131; 382/294

(58) Field of Classification Search .................. 600/407, 600/529, 533; 382/128, 131, 294
See application file for complete search history.

(56) References Cited

U.S. PATENT DOCUMENTS

| 5,633,951 | A  | * | 5/1997  | Moshfeghi ............... 382/294 |
| 2005/0238253 | A1 | * | 10/2005 | Behrenbruch et al. ........ 382/294 |
| 2006/0224363 | A1 | * | 10/2006 | Valadez ................... 702/189 |

OTHER PUBLICATIONS

Boiselle et al. Recent Advances in Central Airway Imaging. Chest 2002; 121; 1651-1660.*
Hutton et al. Software for image registration: Algorithms, accuracy, efficacy; Seminars in Nuclear Medicine, vol. 33, Issue 3, Jul. 2003, pp. 180-192.*
Stern et al., "Normal trachea during forced expiration: Dynamic CT measurements", Radiology, vol. 187, No. 1, 1993, pp. 27-31.
Heussel et al., "Paired inspiratory/expiratory spiral CT and continuous respiration cine CT in the diagnosis of tracheal instability", European Radiology 2001, vol. 11, No. 6, 2001, pp. 982-989.
Abbott et al., "Obstructive sleep apnea: MR imaging volume segmentation analysis", Radiology, vol. 232, No. 3, Sep. 2004, pp. 889-895.

(Continued)

*Primary Examiner* — Brian Casler
*Assistant Examiner* — Phong K Huynh
(74) *Attorney, Agent, or Firm* — Peter Withstandley

(57) ABSTRACT

A method of detecting malacia in airways includes providing a plurality of 3-dimensional (3D) digital lung images acquired over an inhalation/exhalation cycle from a same subject, each said image comprising a set of intensities on a 3-dimensional grid of points, registering a successive pair of images, wherein a registration mapping of the point grid of one image is calculated, locating airways in each of said pair of images, and collecting those points between the airways in each of said pair of images, wherein a volume of said collected points is a measure of an extent of malacia in said airways.

17 Claims, 4 Drawing Sheets

OTHER PUBLICATIONS

McLennan et al., "Assessment of major airway obstruction using image analysis of digital CT information", Proc SPIE Int Soc Opt Eng; Proceedings of SPIE—The International Society for Optical Engineering 1996 Society of Photo-Optical Instrumentation Engineers, Bellingham, WA, vol. 2709, 1996, pp. 197-208.

Bluemke et al., "Volume-preserving nonrigid registration of MR breast images using free-form deformation with an incompressibility constraint", IEEE Transactions on Medical Imaging, IEEE Service Center, Piscatawayu, NJ, vol. 22, No. 6, Jun. 1, 2003, pp. 730-741.

Loeckx et al., "Plaque and stent artifact reduction in subtraction CT angiography using nonrigid registration and a volume penalty", Medical Image Computing and Computer-Assisted Intervention—MIC CAI 2005 Lecture Notes in Computer Science; LNCS, Springer-Verlag, BE, vol. 3750, Jan. 1, 2005, pp. 361-368.

* cited by examiner

SYSTEM AND METHOD FOR AUTOMATIC DETECTION AND MEASUREMENT OF MALACIA IN THE AIRWAYS

CROSS REFERENCE TO RELATED UNITED STATES APPLICATIONS

This application claims priority from "Computer Aided Detection and Measurement of Malacia in the Airways", U.S. Provisional Application No. 60/819,424 of Bogoni, et al., filed Jul. 7, 2006, the contents of which are herein incorporated by reference.

TECHNICAL FIELD

This disclosure is directed to the automatic detection and measurement of the presence of malacia from volumetric images of the thorax acquired at multiple time points during the inspiration/expiration cycle.

DISCUSSION OF THE RELATED ART

Malacia is the effect of softening of tissue. Instances of malacia may appear in the larynx, trachea or bronchi. In the context of the airways, such softening is often connected to a collapse of an airway during the breathing cycle. The key consideration is that in the presence of malacia in the airways, the airways can collapse locally either completely, by closing the airways, or partially, by substantially reducing the cross section of the airways. This can cause poor oxygenation and is of particular concern for asthmatic patients. It also can give rise to sleep apnea and may cause suffocation. It may be the result of a patient being in a prolonged ventilation, or the result of congenital characteristics of the airways tissue.

When malacia is detected, it is often addressed by the introduction of stents to provide structural support to the effected airway. The detection of malacia, achieved by examining computed tomography (CT) or magnetic resonance (MR) imaging, in the area of the main airways is simple if it occurs at a point when the acquisition of the data coincides with a time of collapse of the airways. However, such collapse may occur at a different point in the breathing cycle. For this reason, clinical guidelines suggest that the airways be examined during both a full inspiration and a full expiration. However, as demonstrated in clinical cases, this collapse may occur at intermediary points in the breathing cycles and remain undetected.

Prior art in this area is mostly limited to the analysis of a single image for the localization of the area and determination of the placement of a stent. That can be accomplished by extracting the airways from the image and computing the medial axis transform. By examining the cross-section of the trachea along the airways, it is possible to determine the area and extent of the stricture or stenosis. From this information the type of stent can be determined.

However, if only a portion of the breathing cycle is available, it is possible that either the malacia be missed or mis-estimated.

SUMMARY OF THE INVENTION

Exemplary embodiments of the invention as described herein generally include methods and systems for using multiple volumes of the lungs acquired at different points during the breathing cycles for detecting malacia in the airways. This would enable the automatic analysis of the airways to detect meaningful changes in diameter throughout the airways, upon detection of the change, report its extent and magnitude.

According to an aspect of the invention, there is provided a method for detecting malacia in airways, including the steps of providing a plurality of 3-dimensional (3D) digital lung images acquired over an inhalation/exhalation cycle from a same subject, each said image comprising a set of intensities on a 3-dimensional grid of points, registering a successive pair of images, wherein a registration mapping of the point grid of one image is calculated, locating airways in each of said pair of images, and collecting those points between the airways in each of said pair of images, wherein a volume of said collected points is a measure of an extent of malacia in said airways.

According to a further aspect of the invention, the method comprises calculating a quality factor of said registration mapping, wherein if said quality factor is greater than a predetermined threshold, accepting the registration, otherwise repeating said steps of registering the pair of images and calculating a quality factor until an acceptable registration is calculated.

According to a further aspect of the invention, the registration mapping is a non-rigid registration mapping $\phi$ that changes spatial coordinates corresponding to said point grid $$\begin{pmatrix} x \\ y \\ z \end{pmatrix} \rightarrow \begin{pmatrix} X \\ Y \\ Z \end{pmatrix}$$

from one image to the other defined by $$\begin{cases} X = \phi_x(x, y, z) = x + u_x(x, y, z) \\ Y = \phi_y(x, y, z) = y + u_y(x, y, z), \\ Z = \phi_z(x, y, z) = z + u_z(x, y, z) \end{cases}$$

wherein $u_x$, $u_y$, and $u_z$ are displacements found according to a similarity measure between said pair of images.

According to a further aspect of the invention, the registration mapping is locally rigid.

According to a further aspect of the invention, a determinant $|D\phi|(x, y, z)$ of a Jacobian matrix $D\phi$ of said registration mapping, $$D\phi = \begin{pmatrix} \frac{\partial \phi_1}{\partial x} & \frac{\partial \phi_1}{\partial y} & \frac{\partial \phi_1}{\partial z} \\ \frac{\partial \phi_2}{\partial x} & \frac{\partial \phi_2}{\partial y} & \frac{\partial \phi_2}{\partial z} \\ \frac{\partial \phi_3}{\partial x} & \frac{\partial \phi_3}{\partial y} & \frac{\partial \phi_3}{\partial z} \end{pmatrix},$$

is approximately equal to 1.

According to a further aspect of the invention, the quality factor Q is defined as $$Q = \frac{1}{2} \sum_{i=1}^{2} w_i(\alpha_i),$$

wherein

-continued $$\alpha_1 = \frac{1}{N} \sum_{x,y,z} \min\left(|D\Phi|(x, y, z), \frac{1}{|D\phi|(x, y, z)}\right),$$

$$\alpha_2 = \min_{x,y,z}\left(\min\left(|D\phi|(x, y, z), \frac{1}{|D\phi|(x, y, z)}\right)\right),$$

wherein N is the number points in the grid, and wherein $w_1(\alpha_1)$ and $w_2(\alpha_2)$ are sigmoid weighting functions that monotonically increase from 0 to 1 to penalize abnormal local deformations.

According to a further aspect of the invention, the sigmoid weighting functions are $$w_1(\alpha_1) = \exp(-A(1-\alpha_1)^{E_1}),$$

and $$w_2(\alpha_2) = \exp(-B(1-\alpha_2)^{E_2}).$$

According to a further aspect of the invention, A=B=10, $E_1$=4 and $E_2$=8.

According to a further aspect of the invention, the method comprises registering each successive pair of images in said time series of images, and for each pair with an acceptable registration mapping, growing a volume between the airways in each of said pair of images, and accumulating said volumes over all pairs of successive images.

According to another aspect of the invention, there is provided a method of detecting malacia in airways including providing a pair of 3-dimensional (3D) digital lung images, each said image comprising a set of intensities on a 3-dimensional grid of points, calculating a locally rigid registration mapping $\phi$ that changes spatial coordinates corresponding to said point grid from one image (x,y,z) to the other (X,Y,Z) defined by $$\begin{cases} X = \phi_x(x, y, z) = x + u_x(x, y, z) \\ Y = \phi_y(x, y, z) = y + u_y(x, y, z), \\ Z = \phi_z(x, y, z) = z + u_z(x, y, z) \end{cases}$$

wherein $u_x$, $u_y$ and $u_z$ are displacements found according to a similarity measure between said pair of images, and calculating a quality factor of said registration mapping, wherein if said quality factor is greater than a predetermined threshold, the registration is accepted, and wherein said malacia is found from said registration.

According to a further aspect of the invention, the method comprises providing a plurality of 3-dimensional (3D) digital lung images acquired over an inhalation/exhalation cycle from a same subject and registering each successive pair of images.

According to a further aspect of the invention, the method comprises segmenting airways in each of said pair of images, and growing a volume between the airways in each of said pair of images, wherein said volume is a measure of an extent of malacia in said airways.

According to a further aspect of the invention, the quality factor is defined as $$Q = \frac{1}{2}\sum_{i=1}^{2} w_i(\alpha_i)$$

wherein $$\alpha_1 = \frac{1}{N} \sum_{x,y,z} \min\left(|D\Phi|(x, y, z), \frac{1}{|D\phi|(x, y, z)}\right),$$

$$\alpha_2 = \min_{x,y,z}\left(\min\left(|D\phi|(x, y, z), \frac{1}{|D\phi|(x, y, z)}\right)\right),$$

wherein N is the number points in the grid, wherein $|D\phi|$ is a determinant of a Jacobian matrix of $\phi$, and wherein $w_1(\alpha_1)$ and $w_2(\alpha_2)$ are sigmoid weighting functions that monotonically increase from 0 to 1.

According to another aspect of the invention, there is provided a program storage device readable by a computer, tangibly embodying a program of instructions executable by the computer to perform the method steps for detecting malacia in airways.

DETAILED DESCRIPTION OF EXEMPLARY EMBODIMENTS

Figure 1:
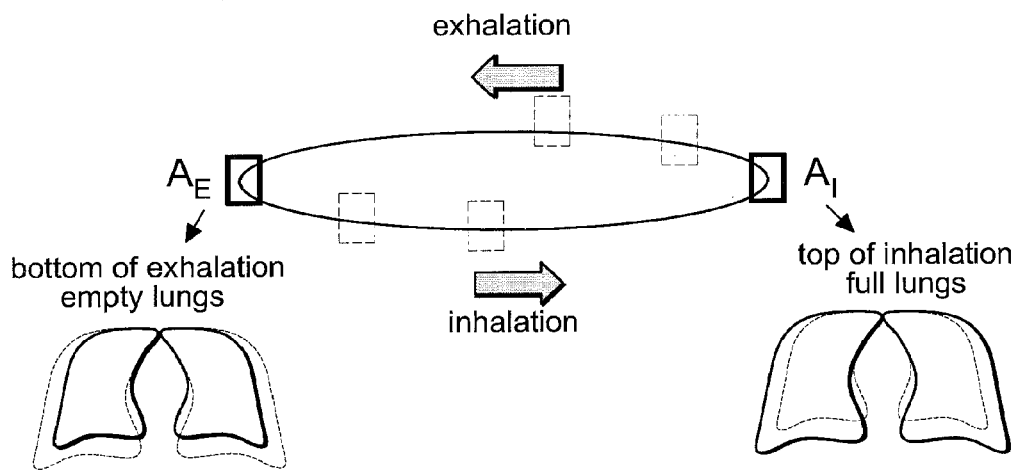
FIG. 1 illustrates the Inhalation/Exhalation cycle, according to an embodiment of the invention.

Exemplary embodiments of the invention as described herein generally include systems and methods for detection of malacia in airways. Accordingly, while the invention is susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention.

As used herein, the term "image" refers to multi-dimensional data composed of discrete image elements (e.g., pixels for 2-D images and voxels for 3-D images). The image may be, for example, a medical image of a subject collected by computer tomography, magnetic resonance imaging, ultrasound, or any other medical imaging system known to one of skill in the art. The image may also be provided from non-medical contexts, such as, for example, remote sensing systems, electron microscopy, etc. Although an image can be thought of as a function from $R^3$ to R, the methods of the inventions are not limited to such images, aid can be applied to images of any dimension, e.g. a 2-D picture or a 3-D volume. For a 2- or 3-dimensional image, the domain of the image is typically a 2- or 3-dimensional rectangular array, wherein each pixel or voxel can be addressed with reference to a set of 2 or 3 mutually orthogonal axes. The terms "digital" and "digitized" as used herein will refer to images or volumes, as appropriate, in a digital or digitized format acquired via a digital acquisition system or via conversion from an analog image.

According to an embodiment of the invention, this disclosure will be discussed with respect to two image volumes acquired at full expiration and inspiration. It is to be understood, however, that this description in terms of these two image volumes is non-limiting and for illustrative purposes only. New technologies, such as 64 slice CT, can be gated to acquire multiple images of the lung during the breathing cycle, perhaps as many as 10 or 15 per cycle, and one of ordinary skill in the art can apply the teachings herein disclosed to use all of these images in the analysis.

FIG. 1 illustrates the breathing cycle with the volumetric changes in the lungs, according to an embodiment of the invention. This drawing shows an ellipse representing the inhalation/exhalation cycle, and shows two points of acquisition: at the top of the inhalation and at the bottom of the exhalation. The label $A_E$ indicates an image/volume acquisition at the bottom of the exhalation process and the label $A_I$ indicates an image/volume acquisition at the top of the inhalation process. The two sketches of the lung are meant to illustrate the change in volume of the lungs. The solid line in each sketch illustrates the size of the lungs at that point in the breathing cycle while the dotted line illustrates the complementary size at the other position of the cycle. Other potential acquisitions are illustrated by the dotted rectangles in the ellipse. If multiple datasets are available it would be matter of extending the process to incorporate these extra datasets.

Since one is primarily looking for substantial changes, the acquisitions could be performed at very low dosages. Potentially the acquisition of the data could be performed over more than one breathing cycle with the patient only partially inhaling or exhaling. The main consideration is that multiple images can be incorporated for automatic detection, analysis and visualization.

Figure 3:
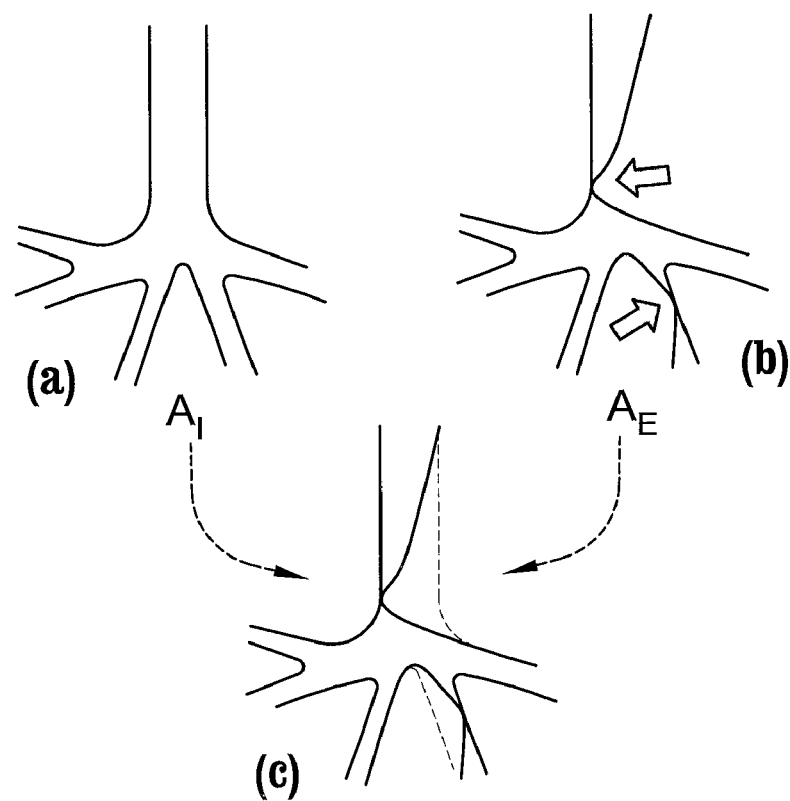
FIGS. 3(a)-(c) illustrates registration of volumetric images, according to an embodiment of the invention.

Thus, following acquisition, the images should be registered to one another, as illustrated in FIGS. 3(a)-(c). Referring to the figure, the FIGS. 3(a) and 3(b), respectively labeled $A_I$ and $A_E$, represent airways during the inhalation/exhalation part of the cycle, respectively, and the arrows illustrate areas of malacia in the airways. Following registration, images $A_I$ and $A_E$ are aligned as illustrated by the bottom middle image, FIG. 3(c). The dotted area illustrates the area that has undergone deformation. The registration quality would improve by incorporating the extra datasets, which would also allow more accurately determination of the presence of malacia and more accurately differentiate the malacia over the normal changes of airways diameter that occur during the breathing cycle.

Figure 4:
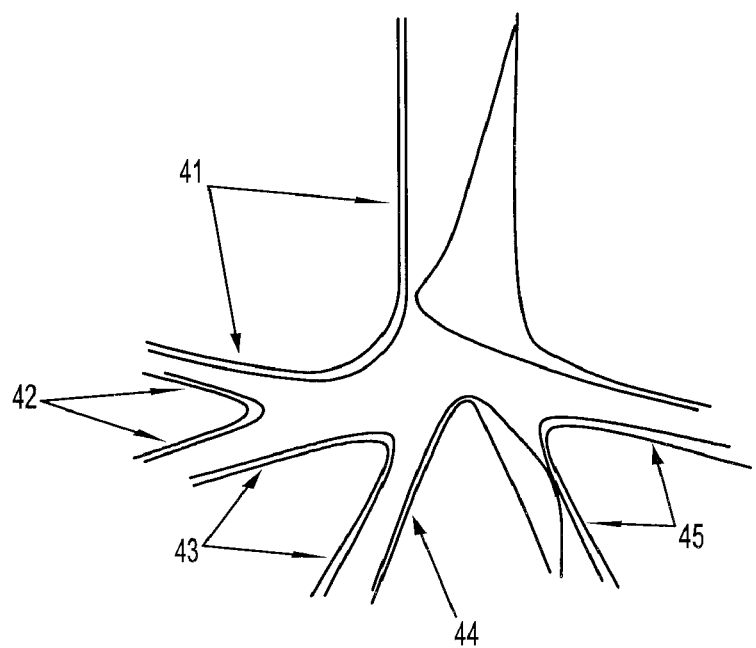
FIG. 4 illustrates registration with residual error, due to elasticity of tissues, according to an embodiment of the invention.

In practice, there could also be a residual error in the registration due to tissue elasticity as shown in FIG. 4. Regions containing residual error, as distinct from regions deformed due to malacia, are indicated by reference numbers 41, 4, 43, 44, and 45. By analyzing the change in airways diameter one can identify areas that have undergone substantial change. This change can be measured by creating a map of the airways which could be visualized by color coding the image at the top of the inhalation with the amount of residual change. Thus, for example, the amount of change could be the color red for a large change decreasing to the color blue to illustrate minimal/no change. Other similar schemes could be used.

Similarly, the change in airways diameter could be displayed in a virtual fly though of the airways to facilitate the localization of the malacia. A virtual fly through generates a virtual endoscopic view of the airways which would enable the physician to notice the protrusion. Although virtual fly throughs of the airways are known in the art, having the ability to identify malacia would enable a visualization which could highlight spots along the virtual fly thru, characterizing and/or coding the extent and possibly the thickness of the connective tissue, which has thinned in the area of malacia.

The type of registration used to accomplish this goal is known as non-rigid, soft-tissue or fluid-like registration. A non-rigid registration process finds a change of spatial coordinates $$\begin{pmatrix} x \\ y \\ z \end{pmatrix} \rightarrow \begin{pmatrix} X \\ Y \\ Z \end{pmatrix}$$

defined by $$\begin{cases} X = \phi_x(x, y, z) = x + u_x(x, y, z) \\ Y = \phi_y(x, y, z) = y + u_y(x, y, z) \\ Z = \phi_z(x, y, z) = z + u_z(x, y, z) \end{cases}$$

where $u_x$, $u_y$, and $u_z$ are the displacements found according to a similarity measure between consecutive images.

Under a change of coordinates $(x,y,z) \rightarrow (\phi_1(x,y,z), \phi_2(x,y,z), \phi_3(x,y,z))$, where $\phi_1$, $\phi_2$ and $\phi_3$ are differentiable functions, the local change of volume at a point is given by the determinant of the Jacobian matrix of the deformation:

$$D\phi = \begin{pmatrix} \frac{\partial \phi_1}{\partial x} & \frac{\partial \phi_1}{\partial y} & \frac{\partial \phi_1}{\partial z} \\ \frac{\partial \phi_2}{\partial x} & \frac{\partial \phi_2}{\partial y} & \frac{\partial \phi_2}{\partial z} \\ \frac{\partial \phi_3}{\partial x} & \frac{\partial \phi_3}{\partial y} & \frac{\partial \phi_3}{\partial z} \end{pmatrix}.$$

When $|D\phi|(x,y,z)=1$, the local change of volume is zero, that is, the transformation neither reduces nor increases the local volume (it is locally rigid). When $|D\phi|(x, y, z)<1$, the transformation is a local compression. Values much smaller than 1 are indicative of a strong local compression of the tissue while values much greater than 1 are also indicative of a large local deformation, and imply that the local volume was largely increased. In fact, one has $$|D\phi^{-1}| = \frac{1}{|D\phi|},$$

where $\phi^{-1}$ is the inverse transformation, which means that large values of $|D\phi|$ make the inverse transformation almost singular.

A desirable properly of a non-rigid deformation is that it stays as close as possible to a rigid deformation, that is, that the values of $|D\phi|(x,y,z)$ stay as close as possible to 1.

The above principles provide means of detecting abnormal deformation areas by measuring how far the actual deformation found by the registration is to the desired situation: an almost rigid deformation. For example, a function to measure such proximity to a locally rigid deformation could be defined as:

$$Q = \frac{1}{2}\sum_{i=1}^{2} w_i(\alpha_i),$$

where $$\alpha_1 = \frac{1}{N}\sum_{x,y,z} \min\left(|D\phi|(x,y,z), \frac{1}{|D\phi|(x,y,z)}\right),$$

where N is the number points in the grid, and $$\alpha_2 = \min_{x,y,z}\left(\min\left(|D\phi|(x,y,z), \frac{1}{|D\phi|(x,y,z)}\right)\right).$$

The two weighting functions $w_1(x)$ and $w_2(x)$ can be chosen to penalize local deformations that are considered abnormal. For example, the weighting functions could be defined as sigmoid functions, for example:

$$w_1(x) = \exp(-10(-1-x)^{E_1}), w_2(x) = \exp(-10(1-x)^{E_2}).$$

Figure 2:
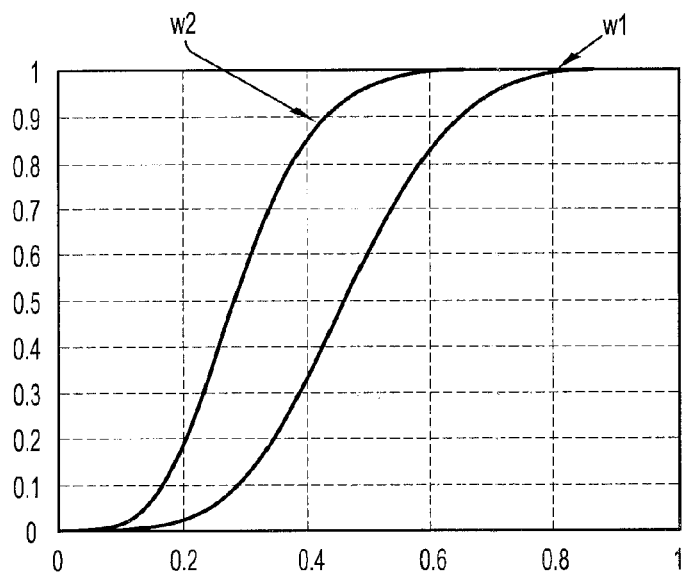
FIG. 2 illustrates two exemplary functions used to weight the coefficient, according to an embodiment of the invention.

Setting the exponents $E_1=4$ and $E_2=8$ yields the sigmoid functions $w_1$ and $w_2$ as plotted in FIG. 2.

Notice that $\alpha_1$ and $\alpha_2$ are related to the determinant of the Jacobian. When the value of $|D\phi|(x,y,z)$ is greater than 1, one considers instead $$|D\phi^{-1}|(x,y,z) = \frac{1}{|D\phi|(x,y,z)},$$

so that one deals only with values between 0 and 1. In this way, $\alpha_1$ represents an average volume distortion, irrespective of it being an increase or decrease in volume, and $\alpha_2$ represents a maximum distortion over the image. Starting with these two values, the weighting functions $w_1$ and $w_2$ can be determined empirically, depending on the application, to penalize values smaller than 1.

The quality factor provides a criterion by which to accept or reject the registration. However, this criterion should be partially adaptive rather than absolute, since lungs and their structure vary substantially from patient to patient. Overall, one standard approach to terminate the process of registration is the termination due to non diminishing residual difference in structures or landmarks between two pair of images.

As stated above, the description of a malacia detection and measurement method in terms of images acquired at the extremes of the inhalation/exhalation cycle is exemplary and for illustrative purposes only. According to another embodiment of the invention, a time series of images acquired over a full inhalation/exhalation cycle is acquired, and the registration described above is performed between each successive pair of images in the time series. A quality of registration may be determined respective to subsequent pair of images. Then, after segmenting each image, region growing can be performed between the volumes of each successive pair of images, and the volume added from each region growing instance can be accumulated over the successive pairs to obtain a total volume difference between the extrema of the cycle.

The registration and its quality help to determine presence or absence of malacia. This disease causes the softening of the tissues that provide structure to the airways, so that when the air pressure and musculature affect the breathing cycle from inhaling to exhaling and vice-versa, sections of airways may collapse closing the area. Hence, registration enables the clinician to determine portions which might differ in proper expansion, while accounting for dilation of the diaphragm, etc.

The airways can be identified by, for example, segmentation. Segmentation and measurement of the extent of the malacia can also be performed automatically by considering the volume of voxels within the two surfaces of the airways at the two acquisition times. First, subtraction of the images before and after registration of the airways is performed to highlight differences. Following subtraction and after filtering for small specs in the subtraction, a region growing, 3D connected components, or any other voxel collecting algorithm can be used to determine potential malacia regions. Regions that are within the airways are those that should be considered, since there might be additional differences in the parenchyma. Malacia can be observed from the subtraction between the before and after registration of the airways. If there is a portion of large difference in the registration that is localized to an area, that is a spot of collapse in one and not in the other. The criteria would be different if there are many images in the time series since the collapse of the airways would not be instantaneous but across the sequence. In that case, one would be observing the trends in the subtraction.

The results of the analysis and measurements can be automatically computed by a computer aided system which can be specifically executed for locating and measuring the amount of malacia present in the airways or be incorporated as a standard/default tool with any application aimed at performing analysis of lungs from multiple images.

Note that segmentation can actually be performed before or after registration, depending on the ability of distributing the computational resources and whether segmentation is a slower process. If it is computed before registration, however, the segmentation will undergo a 3D warp which is the same transformation that brings the two images into registration. Hence, without loss of generality, segmentation can be performed before or after with the caveat of having to introduce the warping. In the subtraction phase, which allows comparison of the segmented structures, the relevant difference between structures before or after registration would be weighted by the quality metric of the registration. Hence, if, for example, the registration would determine that on average a value of K by which the registration is deemed acceptable, the subtraction between the before and after registration of the airways would be subjected to the same criteria.

Figure 5:
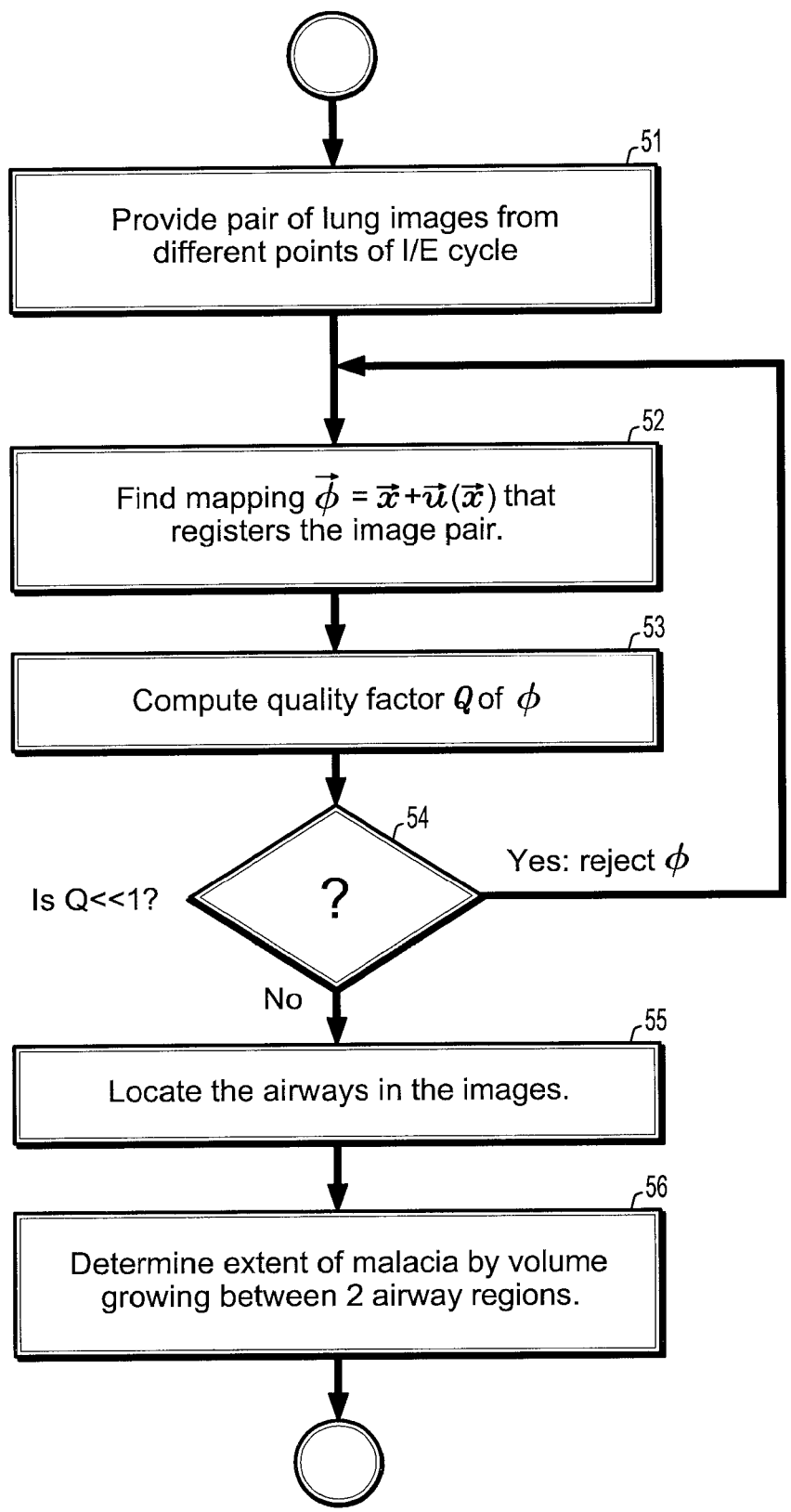
FIG. 5 is a flowchart illustrating an algorithm for detection of malacia in airways, according to an embodiment of the invention.

A flowchart of an algorithm according to an embodiment of the invention for malacia detection in airways is shown in FIG. 5. An algorithm begins at step 51 by acquiring 2 image volumes of the lungs at different times during the inhalation/exhalation cycle. Note that these images can be acquired using any imaging modality, such as computed tomography (CT) or magnetic resonance imaging (MRI). At step 52, a mapping $\vec{\phi} = \vec{x} + \vec{u}(\vec{x})$ that registers the image pair is calculated, where the arrow indicates that $\phi$, u, and x are vectors as described above. At step 53, a quality factor Q of the mapping $\phi$ is calculated, $$Q = \frac{1}{2}\sum_{i=1}^{2} w_i(\alpha_i),$$

where $w_1$, $w_2$, $\alpha_1$, $\alpha_2$ are as defined above. The quality factor Q has been defined to have values between 0 and 1. If, at step 54, Q has been found to be much less than 1, the registration mapping $\phi$ is rejected, and the algorithm returns to step 52 to calculate a new mapping φ. Note that the comparison at step 54 can be with a predetermined threshold ε to in the range 1<<ε<<1 that measures how far the registration can deviate from a rigid registration. If Q indicates that the mapping φ is sufficiently rigid, the airways are located at step 55, and the extent of the malacia in the lung airways can be calculated at step 56 by determining a volume of those voxels in the region between the airways. Alternatively, the airways can be located before performing image registration.

It is to be understood that the present invention can be implemented in various forms of hardware, software, firmware, special purpose processes, or a combination thereof. In one embodiment, the present invention can be implemented in software as an application program tangible embodied on a computer readable program storage device. The application program can be uploaded to, and executed by, a machine comprising any suitable architecture.

Figure 6:
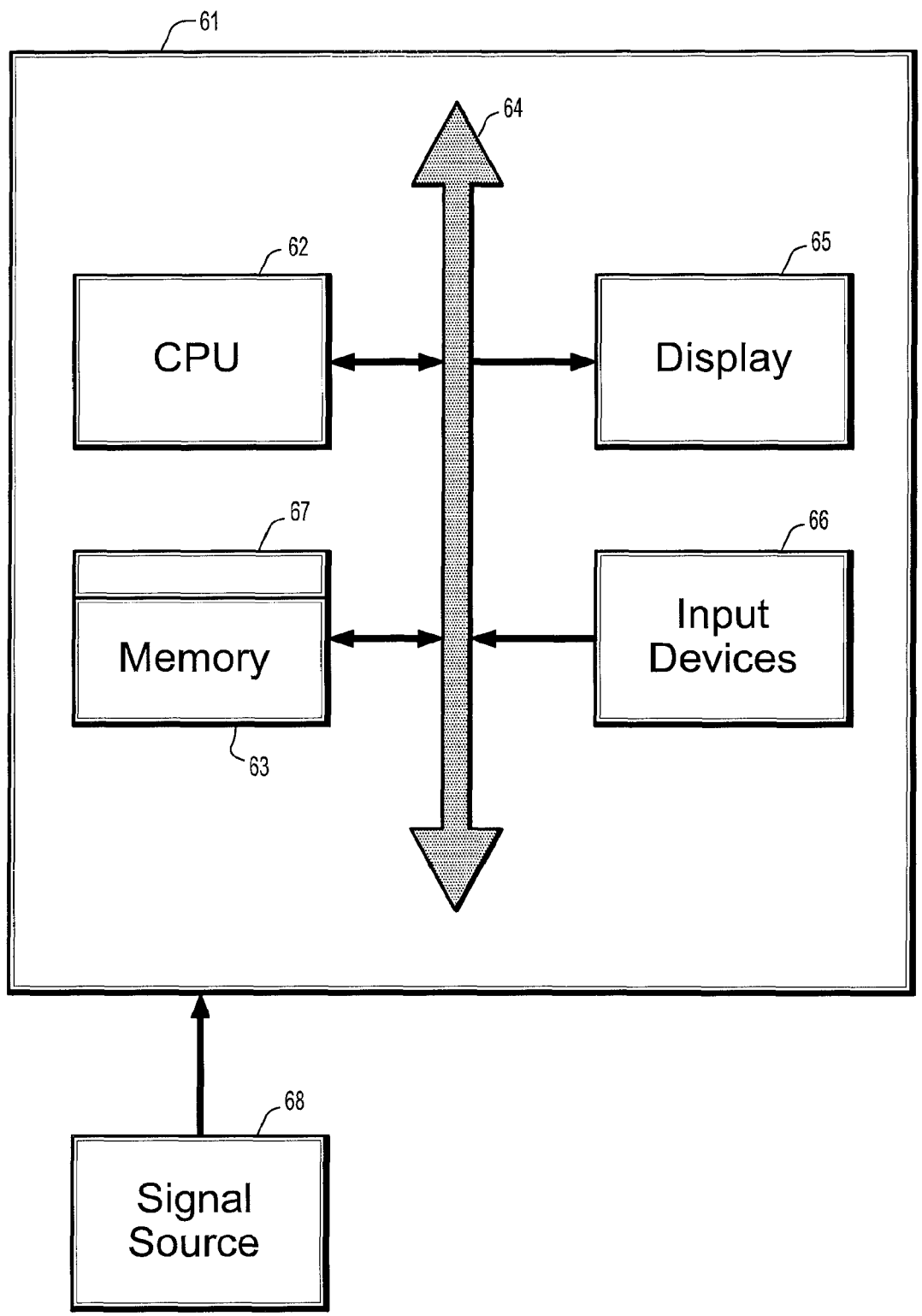
FIG. 6 is a block diagram of an exemplary computer system for implementing an algorithm for detection of malacia in airways, according to an embodiment of the invention.

FIG. 6 is a block diagram of an exemplary computer system for implementing an algorithm for detecting malacia in airways according to an embodiment of the invention. Referring now to FIG. 6, a computer system 61 for implementing the present invention can comprise, inter alia, a central processing unit (CPU) 62, a memory 63 and an input/output (I/O) interface 64. The computer system 61 is generally coupled through the I/O interface 64 to a display 65 and various input devices 66 such as a mouse and a keyboard. The support circuits can include circuits such as cache, power supplies, clock circuits, and a communication bus. The memory 63 can include random access memory (RAM), read only memory (ROM), disk drive, tape drive, etc., or a combinations thereof. The present invention can be implemented as a routine 67 that is stored in memory 63 and executed by the CPU 62 to process the signal from the signal source 68. As such, the computer system 61 is a general purpose computer system that becomes a specific purpose computer system when executing the routine 67 of the present invention.

The computer system 61 also includes an operating system and micro instruction code. The various processes and functions described herein can either be part of the micro instruction code or part of the application program (or combination thereof) which is executed via the operating system. In addition, various other peripheral devices can be connected to the computer platform such as an additional data storage device and a printing device.

It is to be further understood that, because some of the constituent system components and method steps depicted in the accompanying figures can be implemented in software, the actual connections between the systems components (or the process steps) may differ depending upon the manner in which the present invention is programmed. Given the teachings of the present invention provided herein, one of ordinary skill in the related art will be able to contemplate these and similar implementations or configurations of the present invention.

While the present invention has been described in detail with reference to a preferred embodiment, those skilled in the art will appreciate that various modifications and substitutions can be made thereto without departing from the spirit and scope of the invention as set forth in the appended claims.

What is claimed is:

1. A method of detecting malacia in airways, comprising the steps of:

receiving, by a computer system, a plurality of 3-dimensional (3D) digital lung images acquired over an inhalation/exhalation cycle from a same subject, each said image comprising a set of intensities on a 3-dimensional grid of points;

registering, by the computer system, a successive pair of images, wherein a registration mapping of the point grid of one image is calculated;

calculating, by the computer system, a quality factor of said registration mapping, wherein the quality factor is indicative of rigidity of the registration mapping;

locating, by the computer system, airways in each of said pair of images; and if the quality factor indicates that the registration mapping is sufficiently rigid, collecting, by the computer system, points between volumes of the airways in each of said pair of images, wherein the points are used to obtain a volume difference that is a measure of an extent of malacia in said airways;

wherein if said quality factor is greater than a predetermined threshold, accepting the registration, otherwise repeating said steps of registering the pair of images and calculating a quality factor until the quality factor exceeds the predetermined threshold;

wherein said quality factor Q is defined as $$Q = \frac{1}{2}\sum_{i=1}^{2} w_i(\alpha_i),$$

and wherein $w_1(\alpha_1)$ and $w_2(\alpha_2)$ are weighting functions that monotonically increase from 0 to 1 to penalize abnormal local deformations, and are defined as $$w_1(\alpha_1) = \exp(-A(1-\alpha_1)^{E_1}),$$

and $$w_2(\alpha_2) = \exp(-B(1-\alpha_2)^{E_2}).$$

2. The method of claim 1, wherein said registration mapping is a non-rigid registration mapping φ that changes spatial coordinates corresponding to said point grid $$\begin{pmatrix} x \\ y \\ z \end{pmatrix} \rightarrow \begin{pmatrix} X \\ Y \\ Z \end{pmatrix}$$

from one image to the other defined by $$\begin{cases} X = \phi_x(x,y,z) = x + u_x(x,y,z) \\ Y = \phi_y(x,y,z) = y + u_y(x,y,z), \\ Z = \phi_z(x,y,z_,) = z + u_z(x,y,z) \end{cases}$$

wherein $u_x$, $u_y$, and $u_z$ are displacements found according to a similarity measure between said pair of images.

3. The method of claim 2, wherein said registration mapping is locally rigid.

4. The method of claim 2, wherein a determinant |Dφ|(x, y,z) of a Jacobian matrix Dφ of said registration mapping, $$D\phi = \begin{pmatrix} \frac{\partial \phi_1}{\partial x} & \frac{\partial \phi_1}{\partial y} & \frac{\partial \phi_1}{\partial z} \\ \frac{\partial \phi_2}{\partial x} & \frac{\partial \phi_2}{\partial x} & \frac{\partial \phi_2}{\partial z} \\ \frac{\partial \phi_3}{\partial x} & \frac{\partial \phi_3}{\partial y} & \frac{\partial \phi_3}{\partial z} \end{pmatrix},$$

is approximately equal to 1.

5. The method of claim 1, wherein the $\alpha_1$ and $\alpha_2$ are $$\alpha_1 = \frac{1}{N} \sum_{x,y,z} \min\left(|D\phi|(x,y,z), \frac{1}{|D\phi|(x,y,z)}\right),$$

$$\alpha_2 = \min_{x,y,z}\left(\min\left(|D\phi|(x,y,z), \frac{1}{|D\phi|(x,y,z)}\right)\right),$$

wherein N is the number points in the grid.

6. The method of claim 5, wherein $A=B=10$, $E_1=4$ and $E_2=8$.

7. The method of claim 1, wherein the plurality of acquired 3D digital lung images comprises a time series of images, and the method further comprising registering each successive pair of images in said time series of images, and for each pair with an acceptable registration mapping, growing a volume between the airways in each of said pair of images, and accumulating said volumes over all pairs of successive images.

8. A method of detecting malacia in airways, comprising the steps of:

providing a pair of 3-dimensional (3D) digital lung images, each said image comprising a set of intensities on a 3-dimensional grid of points;

registering a successive pair of images by calculating a locally rigid registration mapping $\phi$ that changes spatial coordinates corresponding to said point grid from one image (x,y,z) to the other (X,Y,Z) defined by $$\begin{cases} X = \phi_x(x,y,z) = x + u_x(x,y,z) \\ Y = \phi_y(x,y,z) = y + u_y(x,y,z) \\ Z = \phi_z(x,y,z) = z + u_z(x,y,z), \end{cases}$$

wherein $u_x$, $u_y$ and $u_z$ are displacements found according to a similarity measure between said pair of images; and calculating a quality factor of said registration mapping, wherein if said quality factor is indicates that the registration mapping is sufficiently rigid, the registration is accepted, and wherein said malacia is found from said registration by locating airways in each of said pair of images and collecting points between volumes of the airways, wherein the points are used to obtain a volume difference that is a measure of an extent of malacia in said airways;

wherein said quality factor is defined as $$Q = \frac{1}{2} \sum_{i=1}^{2} w_i(\alpha_i),$$

wherein $$\alpha_1 = \frac{1}{N} \sum_{x,y,z} \min\left(|D\phi|(x,y,z), \frac{1}{|D\phi|(x,y,z)}\right),$$

$$\alpha_2 = \min_{x,y,z}\left(\min\left(|D\phi|(x,y,z), \frac{1}{|D\phi|(x,y,z)}\right)\right),$$

wherein N is the number points in the grid, wherein $|D\phi|$ is a determinant of a Jacobian matrix of $\phi$, and wherein $w_1(\alpha_1)$ and $w_2(\alpha_2)$ are weighting functions that monotonically increase from 0 to 1, and are defined as $$w_1(\alpha_1) = \exp(-A(1-\alpha_1)^{E_1}),$$

and $$w_2(\alpha_2) = \exp(-B(1-\alpha_2)^{E_2}).$$

9. The method of claim 8, further comprising providing a plurality of 3-dimensional (3D) digital lung images acquired over an inhalation/exhalation cycle from a same subject and registering each successive pair of images.

10. The method of claim 9, further comprising segmenting airways in each of said pair of images, and growing a volume between the airways in each of said pair of images, wherein said volume difference is a measure of an extent of malacia in said airways.

11. A non-transitory program storage device readable by a computer, tangibly embodying a program of instructions executable by the computer to perform the method steps for detecting malacia in airways, said method comprising the steps of receiving a plurality of 3-dimensional (3D) digital lung images acquired over an inhalation/exhalation cycle from a same subject, each said image comprising a set of intensities on a 3-dimensional grid of points;

registering a successive pair of images, wherein a registration mapping of the point grid of one image is calculated;

calculating a quality factor of said registration mapping, wherein the quality factor is indicative of rigidity of the registration mapping;

locating airways in each of said pair of images; and if the quality factor indicates that the registration mapping is sufficiently rigid, collecting points between volumes of the airways in each of said pair of images, wherein the points are used to obtain a volume difference that is a measure of an extent of malacia in said airways;

wherein if said quality factor is greater than a predetermined threshold, accepting the registration, otherwise repeating said steps of registering the pair of images and calculating a quality factor until the quality factor exceeds the predetermined threshold wherein said quality factor Q is defined as $$Q = \frac{1}{2} \sum_{i=1}^{2} w_i(\alpha_i),$$

wherein $w_1(\alpha_1)$ and $w_2(\alpha_2)$ are weighting functions that monotonically increase from 0 to 1 to penalize abnormal local deformations, and are defined as $$w_1(\alpha_1) = \exp(-A(1-\alpha_1)^{E_1}),$$

and $$w_2(\alpha_2) = \exp(-B(1-\alpha_2)^{E_2}).$$

12. The computer readable program storage device of claim 11, wherein said registration mapping is a non-rigid registration mapping $\phi$ that changes spatial coordinates corresponding to said point grid $$\begin{pmatrix} x \\ y \\ z \end{pmatrix} \to \begin{pmatrix} X \\ Y \\ Z \end{pmatrix}$$

from one image to the other defined by $$\begin{cases} X = \phi_x(x,y,z) = x + u_x(x,y,z) \\ Y = \phi_y(x,y,z) = y + u_y(x,y,z) \\ Z = \phi_z(x,y,z) = z + u_z(x,y,z), \end{cases}$$

wherein $u_x$, $u_y$ and $u_z$ are displacements found according to a similarity measure between said pair of images.

13. The computer readable program storage device of claim 12, wherein said registration mapping is locally rigid.

14. The computer readable program storage device of claim 12, wherein a determinant $|D\phi|(x,y,z)$ of a Jacobian matrix $D\phi$ of said registration mapping, $$D\phi = \begin{pmatrix} \frac{\partial \phi_1}{\partial x} & \frac{\partial \phi_1}{\partial y} & \frac{\partial \phi_1}{\partial z} \\ \frac{\partial \phi_2}{\partial x} & \frac{\partial \phi_2}{\partial x} & \frac{\partial \phi_2}{\partial z} \\ \frac{\partial \phi_3}{\partial x} & \frac{\partial \phi_3}{\partial y} & \frac{\partial \phi_3}{\partial z} \end{pmatrix},$$

is approximately equal to 1.

15. The computer readable program storage device of claim 11, wherein the $\alpha_1$ and $\alpha_2$ are $$\alpha_1 = \frac{1}{N}\sum_{x,y,z} \min\left(|D\phi|(x,y,z), \frac{1}{|D\phi|(x,y,z)}\right),$$

$$\alpha_2 = \min_{x,y,z}\left(\min\left(|D\phi|(x,y,z), \frac{1}{|D\phi|(x,y,z)}\right)\right),$$

wherein N is the number points in the grid.

16. The computer readable program storage device of claim 15, wherein A=B=10, $E_1$=4 and $E_2$=8.

17. The computer readable program storage device of claim 11, wherein the plurality of acquired 3D digital lung images comprises a time series of images, and the method further comprising registering each successive pair of images in said time series of images, and for each pair with an acceptable registration mapping, growing a volume between the airways in each of said pair of images, and accumulating said volumes over all pairs of successive images.

* * * * *